US008263936B2

(12) United States Patent
Terada et al.

(10) Patent No.: US 8,263,936 B2
(45) Date of Patent: Sep. 11, 2012

(54) TRANSMISSION ELECTRON MICROSCOPE HAVING ELECTRON SPECTROSCOPE

(75) Inventors: Shohei Terada, Hitachinaka (JP); Yoshifumi Taniguchi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 341 days.

(21) Appl. No.: 12/414,883

(22) Filed: Mar. 31, 2009

(65) Prior Publication Data

US 2009/0242766 A1    Oct. 1, 2009

(30) Foreign Application Priority Data

Mar. 31, 2008    (JP) .................................. 2008-089193

(51) Int. Cl.
*G01N 23/00* (2006.01)
*G21K 7/00* (2006.01)
(52) U.S. Cl. ........ 250/311; 250/305; 250/306; 250/307; 250/310; 250/397; 250/491.1
(58) Field of Classification Search .......... 250/305–307, 250/310, 311, 397, 491.1
See application file for complete search history.

(56) References Cited

U.S. PATENT DOCUMENTS

| | | | |
|---|---|---|---|
| 6,690,009 B1* | 2/2004 | Overwijk | ...................... 250/307 |
| 2002/0096632 A1 | 7/2002 | Kaji et al. | |
| 2008/0203296 A1 | 8/2008 | Terada et al. | |

FOREIGN PATENT DOCUMENTS

| | | |
|---|---|---|
| JP | 10-302700 | 11/1998 |
| JP | 2000-113854 | 4/2000 |
| JP | 2002-157973 | 5/2002 |
| JP | 2003-151478 | 5/2003 |

OTHER PUBLICATIONS

Terada, S., Aoyama, T., Yano, F. and Mitsui, Y. "Time-resolved acquisition technique for spatially-resolved electron enrgy-loss spectroscopy by energy-filtering TEM", Journal of Electron Microscopy, vol. 51, pp. 291-296, 2002.*

Kimoto, K. and Matsui, Y., "Software techniques for EELS to realize about 0.3eV energy resolution using 300kV FEG-TEM", Journal of Microscopy, vol. 208, pp. 224 to 228, 2002.*

* cited by examiner

*Primary Examiner* — Jack Berman
*Assistant Examiner* — Meenakshi Sahu
(74) *Attorney, Agent, or Firm* — McDermott Will & Emery LLP

(57) ABSTRACT

A transmission electron microscope is capable of correcting, with high efficiency and high accuracy, an electron energy loss spectrum extracted from each of measured portions included in an electron energy loss spectral image with two axes representing the amount of an energy loss and positional information on a measured portion. The transmission electron microscope has an electron spectroscope and a spectrum correction system. The spectrum correction system corrects a spectrum extracted from each measured portion included in an electron energy loss spectral image acquired from a sample based on a difference between a spectrum extracted from a standard portion of a standard spectral image and a spectrum extracted from a portion different from the standard portion.

7 Claims, 4 Drawing Sheets

TRANSMISSION ELECTRON MICROSCOPE IMAGE

SPECTRAL IMAGE

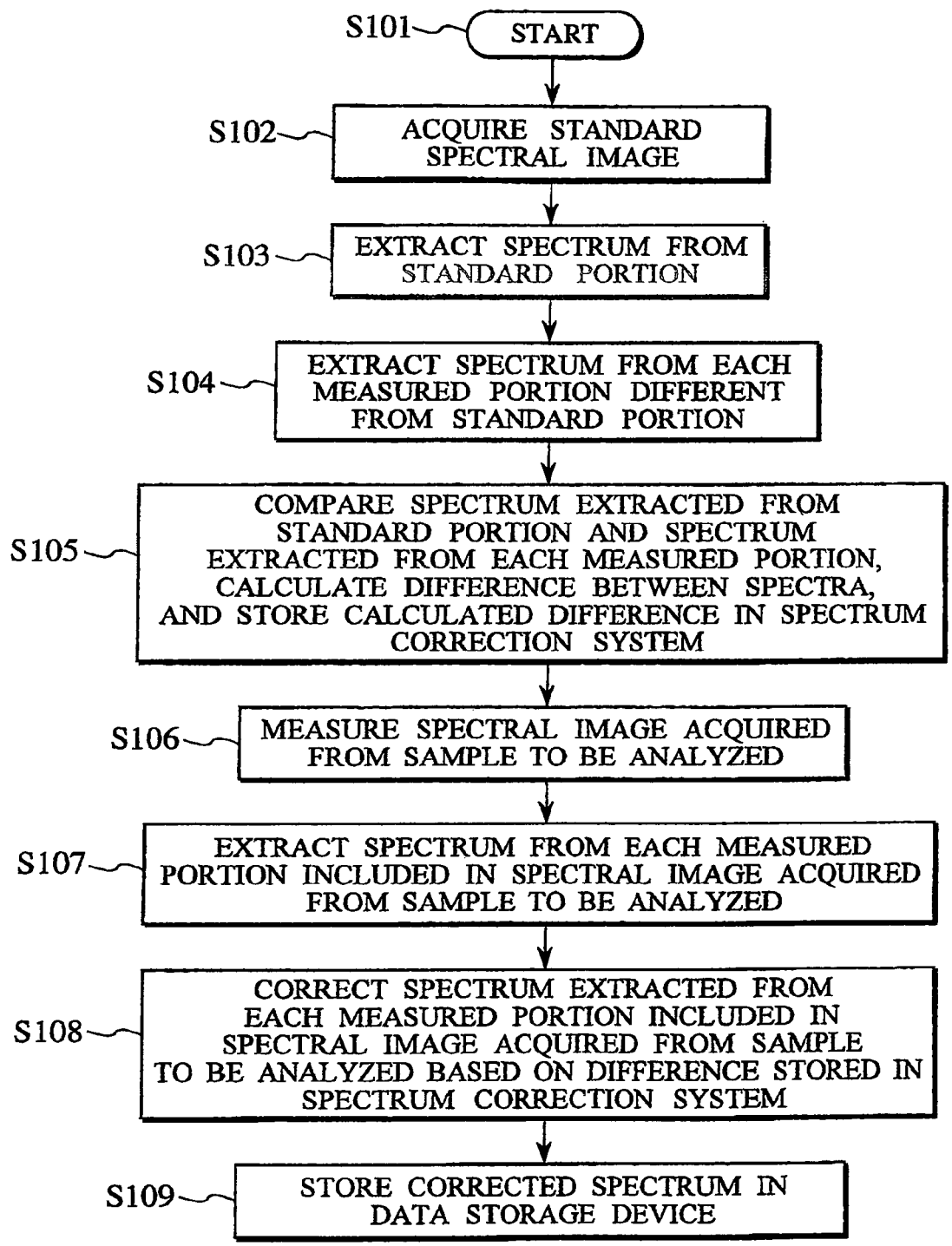

TRANSMISSION ELECTRON MICROSCOPE HAVING ELECTRON SPECTROSCOPE

BACKGROUND OF THE INVENTION

1. Field of the Invention

The present invention relates to a transmission electron microscope having an electron spectroscope that spectrally decomposes an electron beam based on the amount of energy of the electron beam.

2. Description of the Related Art

The sizes of processed silicon semiconductors, the sizes of processed magnetic devices and the like have become minute. Thus, a reduction in degradation of characteristics of devices and a reduction in reliability of the devices are critical issues. In recent years, a two-dimensional element analysis, a spectral analysis using (scanning) transmission electron microscopy ((S)TEM) and a spectral analysis using electron energy loss spectroscopy (EELS) have been required in order to analyze a defect of a nanometer-sized area of a semiconductor device, and find and solve the cause of the defect in a new process for developing a device and in a new process for mass production.

An electron energy loss spectrum is mainly classified into a zero loss spectrum, a plasmon loss spectrum, and a core loss spectrum. The zero loss spectrum is acquired when an electron beam passes through a sample and does not lose its energy. The plasmon loss spectrum is acquired by exciting an electron present in a valence band and reducing energy of the electron. The core loss spectrum is acquired by exciting a core electron and reducing the energy of the electron. In the core loss spectrum, a fine structure is observed in the vicinity of an absorption edge. The fine structure is called an energy loss near-edge structure (ELNES), and has information that includes the state of an electron present in a sample and the state of a chemical bond present in the sample. Since an energy loss value (the position of the absorption edge) varies depending on the element, a qualitative analysis can be carried out. Information related to coordination around a target element can be obtained based on a change (called chemical shift) in the energy loss value. Therefore, a simple state analysis can be carried out.

In a conventional technique, a scanning transmission electron microscope (that uses a scanning coil to scan a sample with a restricted electron beam) and an electron spectroscope (that is capable of spectrally decomposing an electron beam based on the amount of energy of the electron beam) are used to spectrally decompose an electron beam after the electron beam passes through a sample, and to continuously acquire electron energy loss spectra from multiple areas on the sample.

In the above method, however, an aberration of the electron energy loss spectra may occur, or the positions of the origins of the electron energy loss spectra may be different due to a drift of an acceleration voltage applied to the electron beam or due to a change in a magnetic field or in an electric field derived from a change in disturbance occurring around a device. It is, therefore, difficult to compare the shapes of energy loss near-edge structures observed in electron energy loss spectra and compare chemical shifts observed in electron energy loss spectra.

In a technique disclosed in JP-A-2000-113854, a two-dimensional position detection element having pixels measures an electron beam for a short time multiple times, and detects a pixel that indicates a spectrum (of the electron beam) having the maximum intensity based on values detected by the pixels in the multiple measurements. The two-dimensional position detection element then detects a pixel that indicates a spectrum (of the electron beam) having the maximum intensity based on values detected by the pixels in each of the measurements. Then, the two-dimensional position detection element is shifted to ensure that the positions of the pixels, each of which is indicative of the spectrum having the maximum intensity, match each other. In this case, the pixels whose positions match each other are identified as pixels indicative of the same energy value. Thus, a measurement can be carried out for a long time by summing the values detected in the measurements.

In each of techniques disclosed in JP-A-2002-157973 and in JP-A-2003-151478, an electron beam detector detects the peak of a spectrum of an electron beam, and detects a difference between the position of the peak and a standard position on the electron detector. An electron position controller, which controls the position of the electron beam incident on the electron detector, corrects the difference. In addition, while the electron position controller controls the correction of the amount of the change in the position of the peak of the spectrum and a spectrum measurement performed by the electron detector, the electron position controller measures an electron energy loss spectrum.

In the aforementioned techniques, electron energy loss spectra are not acquired simultaneously from multiple points. Thus, when electron energy loss spectra acquired from multiple points are compared, it is difficult to determine whether a shift of a spectrum is derived from a chemical shift (that occurs due to a difference between the states of chemical bonds) or from disturbance. In the techniques, a spectrum used to detect the amount of the change in the position of the peak of the spectrum and a spectrum to be analyzed cannot be necessarily acquired simultaneously. Thus, it is difficult to completely correct the amount of the change in the position of the peak of the spectrum.

JP-A-H10-302700 discloses that although a typical transmission electron microscope sets a focal point of an electron beam focused in the direction of an x axis on a plane and a focal point of the electron beam focused in the direction of a y axis on the same plane to acquire a transmission electron microscope image, a transmission electron microscope described in JP-A-H10-302700 sets a focal point of an electron beam focused in the direction of an x axis on a spectral plane and a focal point of the electron beam focused in the direction of a y axis on an image plane.

As a result, an electron energy loss spectrum acquired from a portion (extending in the direction of the y axis) of the sample can be separated and observed. That is, an image (spectral image) including the spectrum has a stripe pattern corresponding to each laminated layer observed in a transmission electron microscope image shown in FIG. 2A. The image is acquired by an image detector and can be observed as a spectral image with an x axis representing the amount of an energy loss and a y axis representing positional information on the sample, as shown in FIG. 2B. Thus, it is possible to simultaneously observe electron energy loss spectra acquired from different portions of the sample. It is also possible to compare energy loss near-edge structures observed in electron energy loss spectra acquired from different portions of the sample and compare chemical shifts in detail.

The spectral image (disclosed in JP-A-H10-302700) with the x axis representing the amount of the energy loss and with the y axis representing the positional information on the sample is a two-dimensional image. The spectral image disclosed in JP-A-H10-302700 is acquired by an image detector after a condition of a lens such as an electron spectroscope is adjusted and after a focal point of an electron beam focused in the direction of the x axis and a focal point of an electron beam focused in the direction of the y axis are set on different planes. It is therefore possible to simultaneously observe electron energy loss spectra acquired from points in areas (included in the sample and different from each other) that extend in the direction of the y axis.

SUMMARY OF THE INVENTION

It is presupposed that the shapes, positions and the like of spectra included in a zero loss spectral image and acquired from measured points in areas extending in the direction of the y axis are the same and that the shapes, positions and the like of spectra that are included in an electron energy loss spectral image acquired from a sample made of a single type of composition are the same, in order to examine fine structures observed in the spectra and chemical shits due to a difference between that states of chemical bonds based on the electron energy loss spectra acquired from multiple points of the sample to be analyzed.

Therefore, before the electron energy loss spectral image is acquired from the sample to be analyzed, a plurality of lenses provided in the electron spectroscope is adjusted to ensure that the shapes, positions and the like of the spectra included in the zero loss spectral image and acquired from measured points in areas extending in the direction of the y axis are the same or that the shapes, positions and the like of the spectra included in the electron energy loss spectral image acquired from the sample made of a single type of composition are the same. It is, however, difficult to completely match the shapes, positions and the like of the zero loss spectra or completely match the shapes, positions and the like of the electron energy loss spectra acquired from the sample made of a single type of composition when the areas (of the sample) extending in the direction of the y axis are different from each other. In addition, the adjustment of the lenses is complicated, and it may take a long time to adjust the plurality of lenses.

An object of the present invention is to provide a method for correcting, with high efficiency and high accuracy, a spectrum included in an electron energy loss spectral image and acquired from each of multiple points of a sample to be analyzed by means of a transmission electron microscope having an electron spectroscope, and a system and device for the correction.

According to an aspect of the present invention that solves the above problems, a transmission electron microscope has an electron spectroscope and is capable of acquiring a spectral image with an axis representing the amount of an energy loss and an axis representing positional information on a sample. The transmission electron microscope corrects a spectrum extracted from each of measured portions included in an electron energy loss spectral image acquired from the sample to be analyzed based on a difference between a spectrum extracted from a standard portion of a standard spectral image and a spectrum extracted from each of measured portions (that are different from the standard portion) included in the standard spectral image. The standard spectral image represents the amount of an energy loss with an axis and the positional information on the sample with another axis.

In the method for the spectrum correction, it is preferable that the standard spectral image be an zero loss spectral image or an electron energy loss spectral image acquired from a reference sample made of a single type of composition.

According to another aspect of the present invention, a transmission electron microscope has an electron gun, a convergent lens group, an imaging lens group, an image detector, an image display unit, a view field restriction slit, and an electron spectroscope. The electron gun emits an electron beam to a sample. The convergent lens group causes the electron beam emitted by the electron gun to converge. The imaging lens group images the electron beam after the electron beam passes through the sample. The image detector detects the imaged electron beam, i.e., detects an image of the electron beam. The image display unit displays the image detected by the image detector. The view field restriction slit selects a portion (to be observed) of the sample. The electron spectroscope spectrally decomposes the electron beam based on the amount of energy of the electron beam after the electron beam passes through the sample. The transmission electron microscope also has a spectrum correction system and a data storage device. The spectrum correction system corrects a spectrum extracted from each measured portion included in a spectral image. The data storage device stores the corrected spectrum therein. The spectrum correction system uses a standard spectral image to calculate a difference between a spectrum extracted from a standard portion of the standard spectral image and a spectrum extracted from each of measured portions (that are different from the standard portion) in the standard spectral image. Based on the calculated difference(s), the spectrum correction system then corrects an electron energy loss spectral image acquired from the sample to be analyzed. The electron spectroscope outputs a spectral image acquired by setting a focal point of an electron beam focused in an energy dispersion direction (in which energy of the electron beam is dispersed) on a certain plane and setting a focal point of the electron beam focused in a direction perpendicular to the energy dispersion direction on a plane different from the certain plane.

The standard spectral image may be a zero loss spectral image or an electron energy loss spectral image acquired from a reference sample made of a single type of composition. The reference sample made of a single type of composition may be a sample made of a single element such as silicon or nickel. In addition, the reference sample made of a single type of composition may be a sample made of two or more elements such as SiN, SiO or the like. A measurer may set any portion of the standard spectral image as the standard portion. The transmission electron microscope may have a spectrum selection area tool capable of arbitrarily setting the standard portion of the standard spectral image.

The measurer may determine whether or not the spectrum correction system is used. The transmission electron microscope may have a spectrum difference calculation button to cause the spectrum correction system to start to calculate a difference between a spectrum extracted from the standard portion and the spectrum extracted from each of measured portions. In addition, the transmission electron microscope may have a calculation button to calculate the difference between the spectra and a button to start to correct the electron energy loss spectrum.

The method for correcting a spectral image with an axis representing the amount of an energy loss and an axis representing positional information on the sample is to acquire the standard spectral image, acquire a spectral image from the sample to be analyzed, and correct a spectrum extracted from each of measured portions included in the spectral image acquired from the sample to be analyzed based on the difference between the spectrum extracted from the standard portion of the standard spectral image and the spectrum extracted from each of the measured portions (different from the standard portion) included in the standard spectral image. As the standard spectral image, a zero loss spectrum acquired from the sample to be analyzed or a reference sample may be used.

Alternatively, as the standard spectral image, an electron energy loss spectrum acquired from a reference sample made of a single type of composition may be used.

The transmission electron microscope according to the present invention has the electron spectroscope capable of acquiring a spectral image with an axis representing the amount of an energy loss and an axis representing positional information on the sample. The transmission electron microscope according to the present invention also has the spectrum correction system for performing the aforementioned correction.

According to the present invention, the standard spectral image such as a zero loss spectral image or an electron energy loss spectral image acquired from a reference sample made of a single type of composition is acquired; an electron energy loss spectral image is acquired from the sample to be analyzed; and the electron energy loss spectral image acquired from the sample to be analyzed is corrected based on the difference between the spectrum extracted from the standard portion of the standard spectral image and the spectrum extracted from each of the measured portions that are different from the standard portion and included in the standard spectral image. The electron energy loss spectral image is a two-dimensional image having two parameters indicative of the amount of an energy loss and positional information on the sample. The transmission electron microscope having the electron spectroscope is capable of correcting, with high efficiency and high accuracy, a spectrum extracted from each of measured portions included in a spectral image acquired from the sample to be analyzed based on the difference between the spectrum extracted from the standard portion of the standard spectral image and the spectrum extracted from each measured portion of standard spectral image. In addition, the spectrum correction system is capable of correcting, with high efficiency and high accuracy, a spectrum extracted from each of measured portions included in a spectral image acquired by the transmission electron microscope.

According to the present invention, the transmission electron microscope, the method for the spectrum correction, and the spectrum correction system are capable of correcting, with high efficiency and high accuracy, an electron energy loss spectral image with two axes that respectively represent the amount of an energy loss and positional information on a measured portion of the sample.

BRIEF DESCRIPTION OF THE DRAWINGS

Other objects and advantages of the invention will become apparent from the following description of embodiments with reference to the accompanying drawings in which:

FIG. 3 is a flowchart showing a process for correcting a difference between a spectrum extracted from a standard portion and a spectrum extracted from each of measured portions by means of the transmission electron microscope having the electron spectroscope;

DESCRIPTION OF THE PREFERRED EMBODIMENTS

Figure 1:
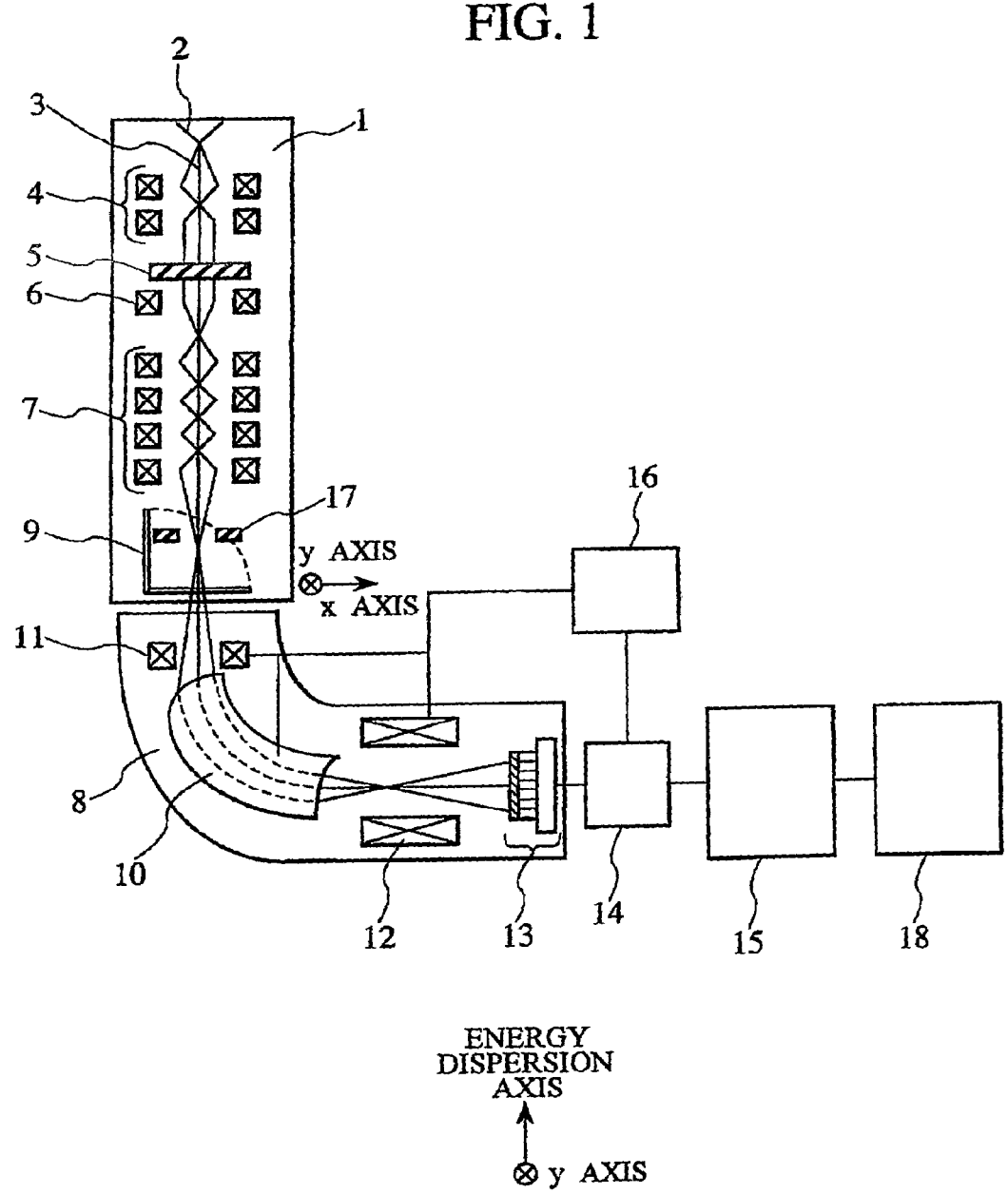
FIG. 1 is an outline diagram showing an example of the configuration of a transmission electron microscope having an electron spectroscope.

The present invention is described below in detail. According to the present invention, a standard spectral image (zero loss spectral image, an electron energy loss spectral image acquired from a reference sample composed of a single type of composition) is first acquired. Zero loss spectra acquired from multiple areas extending in the direction of a y axis have the same half widths in predetermined energy ranges in an energy dispersion direction even when the sample has portions made of respective compositions different from each other or has layers that are made of respective components different from each other. Electron energy loss spectra acquired from multiple portions of a reference sample made of a single type of composition have the same shape in predetermined energy ranges in an energy dispersion direction when the spectra are observed in the same manner. Different aberrations are applied to respective portions of the standard spectral image in this step. The spectra may be displayed with different amounts of energy losses or with different peak half widths even the sample is made of a single type of composition. Correction information on how to correct a spectrum based on each piece of positional information is calculated by using the standard spectral image.

In addition, an electron energy loss spectral image is acquired from the sample to be analyzed without fine adjustment of a spectrum. Thus, the electron energy loss spectral image has an aberration (a distortion and a shift of a half width) in each portion of the spectral image. After the electron energy loss spectral image is acquired, the aberration of the acquired electron energy loss spectral image is corrected. For example, a zero loss spectrum is used as a standard spectrum. Based on the position of the peak of the zero loss spectrum and the shape of the zero loss spectrum, all portions of the spectral image are corrected. When the zero loss spectrum is adjusted before a measurement of a spectral image, accuracy of analysis of the electron microscope can be improved. As the standard spectrum used to correct the aberration, a spectrum acquired from a portion of a compound (including another portion that is to be analyzed) may be used instead of the zero loss spectrum.

The correction of the electron energy loss spectrum may be performed before or after the electron energy loss spectrum is acquired from the sample to be analyzed. It is preferable that the electron microscope have a correction start button to correct the spectrum in order to allow a measurer to arbitrarily set a time point for the correction.

A standard portion used to calculate correction information can be arbitrarily selected from the standard spectral image by the measurer. It is preferable that the electron microscope have a spectrum area selection tool. Therefore, an operator can specify any area in the standard spectral image as the standard portion while viewing an electron microscope image, an electron energy loss spectral image and the like.

According to the present invention, the electron energy loss spectral image can be corrected by means of the correction information stored in a spectrum correction system. In addition, the efficiency of a measurement of the electron energy loss spectral image can be improved by means of the correction information. A time-dependent change, a change in a measurement condition and the like may occur. Thus, it is preferable that the standard spectral image be measured in each of measurements of electron energy loss spectral images in order to perform the measurements with high accuracy.

Since the electron energy loss spectral image acquired the sample to be analyzed is corrected by means of the correction information calculated based on the standard spectral image, the standard spectral image and the electron energy loss spectral image (acquired from the sample to be analyzed) can be acquired without a fine adjustment of a zero loss spectrum before the measurement of the electron energy loss spectral image. In a method for correcting the electron energy loss spectral image, the fine adjustment of the zero loss spectrum and an adjustment of a lens are not required. Therefore, the measurement is easy and does not take a long time.

Embodiment

An embodiment of the present invention is described below with reference to the accompanying drawings. In all of the accompanying drawings used to explain the embodiment, the same elements are denoted by the same reference numerals in principle, and duplicate description is omitted.

FIG. 1 is an outline diagram showing an example of the configuration of a transmission electron microscope having an electron spectroscope according to an embodiment of the present invention.

The transmission electron microscope according to the embodiment is provided with the electron spectroscope and has a transmission electron microscope 1, an electron spectroscope 8, an image display unit 14, a central control unit 16, a spectrum correction system 15 and the like. The transmission electron microscope 1 includes an electron source 2, a convergent lens 4, an objective lens 6, an imaging lens system 7, and a fluorescent plate 9. A sample 5 is placed between the convergent lens 4 and the objective lens 6. The electron spectroscope 8 has a magnetic field sector 10, multipole lenses 11, 12, and an image detector 13 and the like.

The configuration of the transmission electron microscope 1 and the configuration of the electron spectroscope 8 are not limited to the configurations shown in FIG. 1. For example, the electron spectroscope 8 may be provided in the transmission electron microscope 1.

In the transmission electron microscope 1 provided with the electron spectroscope 8, an electron beam 3 is emitted by the electron source 2, passes through the convergent lens 4, and is incident on the sample 5. Then, the electron beam 3 passes through the sample 5, and passes through the imaging lens system 7 composed of a plurality of lenses. When the fluorescent plate 8 is open, the electron beam 3 enters the electron spectroscope 5. After that, the electron beam 3 passes through the multipole lenses 11, 12 and the magnetic field sector 10. The multipole lenses 11, 12 are used for focusing, enlargement, reduction, reduction in aberration, and the like of an electron energy loss spectrum and transmission electron microscope image in the electron spectroscope 8. After the electron beam 3 passes through the magnetic field sector 10, the electron beam 3 is imaged as a transmission electron microscope image, a two-dimensional element distribution image, a spectral image or the like. The image is displayed by the image display unit 14. The magnetic field sector 10 and the multipole lenses 11, 12 are controlled by the central control unit 16. The central control unit 16 is capable of switching between image acquisition modes which are a mode for acquiring a transmission electron microscope image, a mode for acquiring a two-dimensional element distribution image, and a mode for acquiring a spectral image. In addition, the central control unit 16 is capable of changing a focal point of the electron beam to be focused in the directions of x and y axes, i.e., capable of switching between the mode for acquiring a transmission electron microscope image and the mode for acquiring a spectral image.

In the case where the spectral image is acquired, a visual field restriction slit 17 is inserted in order to restrict an area in which the spectrum is acquired, as shown in FIG. 1. The visual field restriction slit 17 has a short length in the direction of the x axis and a long length in the direction of the y axis. The x axis is parallel to an energy dispersion direction in which energy of the electron beam is dispersed. The y axis is parallel to a direction in which the sample is measured. In FIG. 1, the direction of a normal to the surface of the paper sheet showing FIG. 1 indicates the direction of the y axis, and the direction extending between the left and right sides of the paper sheet showing FIG. 1 indicates the direction of the x axis. When the energy of the electron beam 3 that passes through the slit 17 as shown in FIG. 1 is dispersed in a direction perpendicular to the y axis, the energy of the electron beam is dispersed at the image detector 13 in a direction extending between the top and bottom of the paper sheet showing FIG. 1.

Before a spectral image to be analyzed is acquired from the sample 5, a difference between a spectrum extracted from the standard portion of the standard spectral image and a spectrum extracted from each of measured portions (different from the standard portion) of the standard spectral image is calculated by the spectrum correction system 15 based on the zero loss spectral image that is the standard spectral image or on an electron energy loss spectral image acquired from the same sample. Then, the calculated difference is stored in the spectrum correction system 15. After that, a spectral image is acquired from a portion (to be analyzed) of the sample 5 by the image detector 13. Then, the spectrum correction system 15 corrects the spectral image acquired from the portion (to be analyzed) of the sample 5 by the image detector 13 based on the difference stored in the spectrum correction system 15. The corrected spectral image is then stored in a data storage device 18.

FIG. 3 is a flowchart showing a process for correcting a difference (calculated based on the spectral image) between the spectrum extracted from the standard portion and a spectrum extracted from each of measured portions (different from the standard portion) by means of the spectrum correction system 15. The zero loss spectral image or the electron energy loss spectral image is used as the standard spectral image in order to correct the spectrum extracted from each of the measured portions. A zero loss spectrum acquired when an electron beam passes through a sample and does not lose its energy, or an electron energy loss spectral image acquired from a reference sample such as a silicon substrate having a composition uniform in a direction in which the sample is measured, is used to correct a spectrum extracted from each measured portion included in the standard spectral image.

The standard spectral image, which is used to correct a spectrum, is acquired by the image detector 13 based on a spectral image with two axes, and stored in the spectrum correction system 15 in steps S101 and S102. One of the two axes of the spectral image represents the amount of an energy loss of the electron beam at the electron spectroscope 8. The other of the two axes of the spectral image represents positional information. The amount of the energy loss of the electron beam at the electron spectroscope 5 is acquired by the transmission electron microscope having the electron spectroscope. The standard spectral image acquired in the step S102 may be the zero loss spectral image acquired when the electron beam passes through the sample without energy loss or may be a zero loss spectral image acquired when the electron beam passes through an area in which the sample is not present. Alternatively, the standard spectral image acquired in the step S102 may be an electron energy loss spectral image acquired from a reference sample made of a single type of composition located in an area extending in a direction in which the sample is measured.

As the standard spectral image acquired in the step S102, either one of the zero loss spectral image and the electron energy loss spectral image is acquired. It is not necessary to acquire both the zero loss spectral image and the electron energy loss spectral image.

Next, a spectrum is extracted from the standard portion in the direction (of the stored standard spectral image) in which the sample is measured in step S103. In addition, a spectrum is extracted from each of the measured portions different from the standard portion in step S104.

After the spectrum is extracted from each of the measured portions, the spectrum correction system 15 calculates the difference between the spectrum extracted from the standard portion and the spectrum extracted from each of the measured portions by comparing the shape and position of the spectrum extracted from each of the measured portions with the shape and position of the spectrum extracted from the standard portion, and stores the calculated differences therein in step S105.

In step S105, any portion in the standard spectral image may be selected as the standard portion. In addition, the spectrum correction system 15 may calculate a difference between the spectrum extracted from each of the measured portions and an acquired standard spectrum other than the spectrum extracted from the standard portion of the standard spectral image, and store the calculated difference therein.

After the standard spectral image is acquired, and after the sample 5 is moved to ensure that a portion (to be analyzed) of the sample 5 can be analyzed, the image detector 13 acquires a spectral image corresponding to an energy area required to be measured in step S106. After that, a spectrum is extracted from each of the measured portions included in the acquired spectral image in step S107.

The spectra extracted from measured portions of the sample to be analyzed are corrected based on the differences (between the spectrum extracted from the standard portion and the spectra extracted from the measured portions) stored in the spectrum correction system 15 in step S108. The corrected spectra are stored in the data storage device 18 in step S109.

In the flowchart showing the process for correcting the spectral image, the difference between the spectrum extracted from the standard portion of the standard spectral image and the spectrum extracted from each measured portion (different from the standard portion) is calculated and stored, and the spectral image is acquired from the sample to be analyzed and corrected based on the difference between the spectrum extracted from the standard portion of the standard spectral image and the spectrum extracted from each measured portion. However, after the standard spectral image is acquired, the following may be performed: the difference between the spectrum extracted from the standard portion of the standard spectral image and the spectrum extracted from each measured portion is calculated immediately after the spectral image is acquired from the sample to be analyzed; and the spectral image acquired from the sample to be analyzed is corrected.

It is preferable that the standard spectral image be acquired in the process for correcting a spectral image immediately before the spectral image is acquired from the sample to be analyzed. When the standard spectral image does not significantly vary, it is not necessary that the standard spectral image be acquired for each measurement and for each sample.

Figure 4:
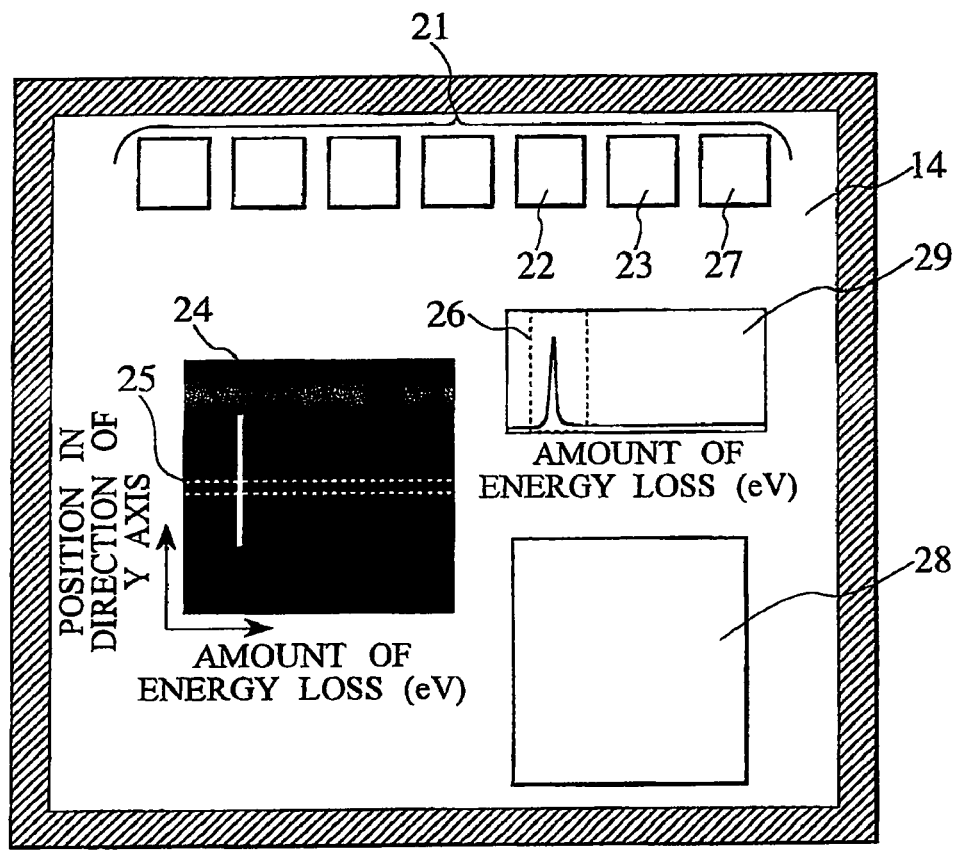
FIG. 4 is a diagram showing an example of a screen of an image display unit provided in the transmission electron microscope having the electron spectroscope.

Next, an operation performed by an operator and an operation guidance screen of the transmission electron microscope having the electron spectroscope are described below. FIG. 4 is a diagram showing an example of the screen of the image display unit 14. A selection button group 21 includes a spectrum acquisition start button 27, a spectrum acquisition termination button, a spectrum acquisition time change button, a spectrum difference calculation button 22, and a spectrum correction button 23. For example, when the spectrum acquisition start button 27 of the selection button group 21 is selected, a zero loss spectral image 24 acquired by the image detector 13 is displayed by the image display unit 14. In this case, an electron energy loss spectral image may be displayed.

When the spectrum difference calculation button 22 of the selection button group 21 is selected, a spectrum selection area tool 25 is displayed in the zero loss spectral image 24, and a spectrum 29 extracted by the spectrum selection area tool 25 and a parameter input map 28 are displayed in the screen of the image display unit 14. The spectrum selection area tool 25 can be moved in the zero loss spectral image 24 in the direction (of the y axis) in which the sample is measured. The width (measured in the direction of the y axis) of the spectrum selection area tool 25 can be changed. Thus, a spectrum can be acquired from any standard portion by means of the spectrum selection area tool 25.

Each of the buttons of the selection button group 21 can be moved and placed at any location in the screen of the image display unit 14. Each of the buttons of the selection button group 21 may be a tool bar. In addition, the spectral image 24, the spectrum 29, the parameter input map 28 and the like, which are displayed in the image display unit 14, can be placed at any location in the screen of the image display unit 14.

In the parameter input map 28, it is possible to set and confirm the position of the standard spectrum. In addition, it is possible to input another standard spectrum in the parameter input map 28. Also, it is possible to set an area of the spectrum extracted from each of the measured portions. Furthermore, it is possible to set an area used to calculate the difference between the spectrum extracted from the standard portion and the spectrum extracted from each of the measured portions. The area set to calculate the difference between the spectrum extracted from the standard portion and the spectrum extracted from each of the measured portions can be set by means of a difference calculation area tool 26 displayed in the spectrum 29.

After all the settings are completed, and when a setting confirmation button located in the parameter input map 28 is selected, the spectrum extracted from each of the measured portions is compared with the spectrum extracted from the standard portion. Then, the difference between the spectrum extracted from each of the measured portions and the spectrum extracted from the standard portion is calculated based on the comparison. The calculated differences are stored in the spectrum correction system 15.

Next, the positions, half widths and shapes of the spectra are described below as examples in terms of the method for calculating the difference between the spectrum extracted from the standard portion and the spectrum extracted from each of the measured portions.

In order to calculate the difference between the position of the zero loss spectrum extracted from the standard portion set by the spectrum selection area tool 25 and the position of the zero loss spectrum extracted from each of the measured portions, the maximum peak intensity of each of the spectra and an energy value corresponding to each of the maximum peak intensities are first calculated as the simplest method. Then, a difference between the energy value of the zero loss spectrum extracted from the standard portion and having the maximum peak intensity and the energy value of the zero loss spectrum extracted from each of the measured portions and having the maximum peak intensity is calculated as the difference between the position of the zero loss spectrum extracted from the standard portion and the position of the zero loss spectrum extracted from each of the measured portions.

Next, a difference between the half width of the spectrum extracted from the standard portion and the half width of the spectrum extracted each of the measured portions is calculated as follows. In the first step of the calculation of the difference between the half widths, the half of the maximum peak intensity of the zero loss spectrum extracted from the standard portion is calculated. In the second step, energy values of the spectrum having approximately the half of the maximum peak intensity are calculated. In this case, one of the energy values of the spectrum having approximately the half of the maximum peak intensity is higher than the energy value of the spectrum having the maximum peak intensity, and the other of the energy values is lower than the energy value of the spectrum having the maximum peak intensity. In the third step, the lower energy value of the spectrum having approximately the half of the maximum peak intensity is subtracted from the higher energy value of the spectrum having approximately the half of the maximum peak intensity to calculate the half width of the spectrum. In the fourth step, the half width of the spectrum extracted from each of the measured portions is calculated according to the first and third steps. In the fifth step, the differences between the half width of the spectrum extracted from the standard portion and the half widths of the spectra acquired from the measured portions are sequentially calculated. The process for calculating the differences between the half widths is an example of the method for calculating the differences between the half widths of the zero loss spectra. The method for calculating the differences between the half widths of the zero loss spectra is not limited to the aforementioned process for calculating the differences between the half widths.

Next, a difference between the shape of the zero loss spectrum extracted from the standard portion and the shape of the zero loss spectrum extracted from each of the measured portions is calculated as follows. In the first step of the calculation of the difference between the shapes, the maximum peak intensity of the zero loss spectrum extracted from the standard portion is calculated. In the second step, the calculated maximum peak intensity is evenly divided into several intensity values. Then, energy values of the spectrum, which correspond to the evenly divided intensity values, are calculated. In this case, one of the energy values of the spectrum, which corresponds to one of the evenly divided intensity values, is higher than the energy value of the spectrum having the maximum peak intensity. The other of the energy values of the spectrum, which corresponds to the one of the evenly divided intensity values, is lower than the energy value of the spectrum having the maximum peak intensity. In the third step, a difference between the higher energy value of the spectrum having the one of the evenly divided intensity values and the energy value of the spectrum having the maximum peak intensity, and a difference between the lower energy value of the spectrum having the one of the evenly divided intensity values and the energy value of the spectrum having the maximum peak intensity, are calculated for each of the evenly divided intensity values. In the fourth step, the shape of the zero loss spectrum extracted from each of the measured portions is calculated in the same manner as the shape of the zero loss spectrum extracted from the standard portion, and the differences between the shape of the zero loss spectrum extracted from the standard portion and the shapes of the zero loss spectra acquired from the measured portions are sequentially calculated.

In the process for calculating the difference between the shapes of the spectra, the maximum peak intensity is evenly divided into several intensity values. The larger the number of the divided intensity values is, the higher the accuracy of the calculation of the differences between the shapes of the spectra is. The process for calculating the difference between the shapes of the spectra is an example of the method for calculating a difference between the shape of the zero loss spectrum extracted from the standard portion and the shape of the zero loss spectrum extracted from each of the measured portions. The method for calculating a difference between the shape of the zero loss spectrum extracted from the standard portion and the shape of the zero loss spectrum extracted from each of the measured portions is not limited to the aforementioned process for calculating the difference between the shapes of the spectra.

The aforementioned methods for calculating the differences between the spectra are simple. However, it is difficult to calculate a difference between spectra indicated by pixel portions that are smaller than a single pixel in the image. In order to calculate a difference between more detailed spectra, a curve fitting method may be used. A function used for the curve fitting method may be a Gaussian function, a Lorenz function, a pseudo-Voigt function (that is used in consideration of an asymmetrical property) or the like. The function used for the curve fitting method, however, is not limited to the above functions.

After the difference between the spectrum extracted from the standard portion and the spectrum extracted from each of the measured portions is calculated, the sample 5 is moved to ensure that a portion (to be analyzed) of the sample 5 can be analyzed. After that, when the spectrum acquisition start button 27 is selected, a spectral image corresponding to an energy area required to be measured is acquired. Then, the spectral image corresponding to the energy area required to be measured is displayed by the image display unit 14. After the spectral image is displayed, and when the spectrum correction button 23 of the selection button group 21 is selected, a spectrum included in the displayed spectral image is corrected based on the difference(s) (between the spectra) stored in the spectrum correction system 15. The corrected spectrum is stored in the data storage device 18. The corrected spectral image or the corrected spectrum may be displayed by the image display unit 14 immediately after the correction. Alternatively, the corrected spectral image or the corrected spectrum may not be displayed when it is not necessary to display the corrected spectral image or the corrected spectrum. The sample 5 may be moved to ensure that a portion (to be analyzed) of the sample 5 can be analyzed before the difference between the spectrum extracted from the standard portion and the spectrum extracted from each of the measured portions is calculated, and then the spectral image corresponding to the energy area to be measured may be acquired.

Next, a detailed example of the correction of the spectrum shown in the spectral image is described below. In the detailed example, the transmission electron microscope 1 having the electron spectroscope 8 is used to perform the correction, and the spectrum correction system 15 according to the present invention is used to correct the position of the spectrum.

In the detailed example, in order to acquire the spectral image, an acceleration voltage of the transmission electron microscope is set to 197 kV; an angle formed between the direction of incidence of the electron beam on the surface of the image detector 13 and a normal to the surface of the image detector 13 is set to 4.4 mrad, and energy dispersion is set to 0.05 eV per pixel. The image detector 13 used to acquire the spectral image is a two-dimensional detector having 1024 pixels×1024 pixels. Observation magnification on a display of the transmission electron microscope is set to 10000 times.

In the case where the observation magnification of the transmission electron microscope was set to 10000 times, an image resolution of the spectral image acquired by the image detector 13 is 0.2 nm per pixel.

First, the sample 5 is moved outside a path of propagation of the electron beam 3. Then, the electron beam 3 passes through the multipole lenses 11, 12 provided in the electron spectroscope 8, and is detected by the image detector 13. With reference to a zero loss spectral image displayed by the image display unit 14, the multipole lenses 11, 12 are adjusted for the optimal conditions. After that, the spectrum acquisition start button 27 is selected to cause the image detector 13 to acquire the standard zero loss spectral image 24. The length of the zero loss spectral image 24 in the direction (in which the sample is measured) of the y axis is a distance corresponding to 600 pixels. The standard portion is regarded as the center line (corresponding to the 300th pixel row) of the zero loss spectral image 24 in the direction of the V axis. The zero loss spectrum 29 is extracted from the standard portion. In addition, the zero loss spectrum is extracted from each of the measured portions. One of the measured portions is located 50 pixel rows above the standard portion, and the other of the measured portions is located 100 pixel rows above the standard portion (actual distances (between the standard portion and the measured portions) calculated based on the image resolution are 10 nm and 20 nm).

Next, the spectrum difference calculation button 22 is selected to calculate the difference between the spectrum extracted from the standard portion and the spectrum extracted from each of the measured portions. According to the embodiment of the present invention, the curve fitting method is used to calculate the difference between the zero loss spectrum extracted from the standard portion and the zero loss spectrum extracted from each of the measured portions. A function used in the curve fitting method is a pseudo-Voigt function. As a result of the calculation of the difference between the zero loss spectrum extracted from the standard portion and the zero loss spectrum extracted from each of the measured portions through the curve fitting method, the shapes and half widths of the zero loss spectra acquired from the portions that are located 50 pixels rows above the standard portion and located 100 pixel rows above the standard portion are the same as the shape and half width of the spectrum extracted from the standard portion. However, the positions of the zero loss spectra acquired from the portions that are located 50 pixels rows above the standard portion and located 100 pixel rows above the standard portion are shifted from the position of the spectrum extracted from the standard portion. The differences from the position of the spectrum extracted from the standard portion and the positions of the spectra acquired from the measured portions are 0.5 eV and −0.3 eV, respectively.

Figure 5:
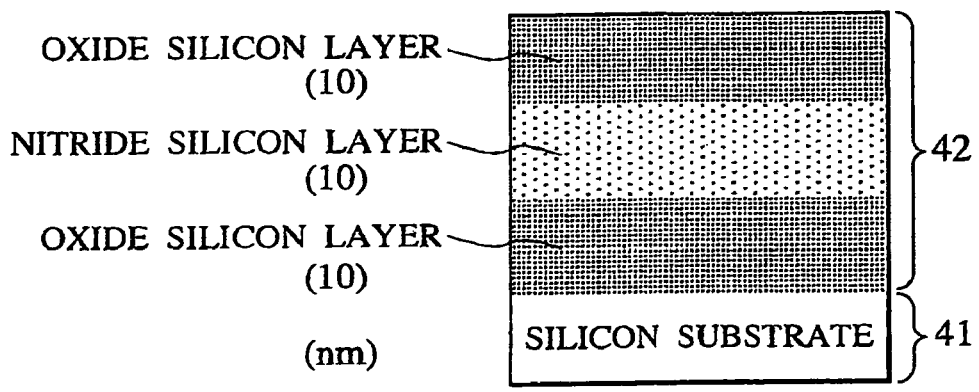
FIG. 5 is an outline diagram showing a sample used for analysis.

Next, the sample 5 is moved to ensure that a desired portion of the sample 5 can be analyzed. After that, the spectrum acquisition start button 27 is selected to acquire the electron energy loss spectral image. FIG. 5 is a schematic diagram showing the sample used for the analysis. The sample 5 has a substrate 41 and a plurality of layers 42. The substrate 41 is made of silicon. The plurality of layers 42 are an oxide silicon layer (having a thickness of 10 nm), a nitride silicon layer (having a thickness of 10 nm) and an oxide silicon layer (having a thickness of 10 nm). The oxide silicon layer, the nitride silicon layer and the oxide silicon layer are sequentially formed on the substrate 41. The acquired electron energy loss spectral image indicates the proximity of an L shell absorption edge of silicon.

The electron energy loss spectral image is acquired to ensure that a spectrum acquired from the substrate 41 is extracted from the center line of the electron energy loss spectral image in the direction (in which the sample is measured) of the y axis, i.e., from the standard portion. As a result, an electron energy loss spectrum acquired from the oxide silicon layer is extracted from the measured portion located 50 pixel rows above the standard portion, and an electron energy loss spectrum acquired from the nitride silicon layer is extracted from the measured portion located 100 pixel rows above the standard portion.

Then, the spectrum correction button 23 is selected to correct the difference between the spectrum extracted from the standard portion and the spectrum extracted from each of the measured portions. Since the electron energy loss spectrum acquired from the silicon substrate 41 is extracted from the standard portion, an absolute value corresponding to the position of a rising edge of the electron energy loss spectrum is corrected based on the position of the peak obtained by photoelectron spectroscopy. The amount of a chemical shift at each position is calculated. As a result, the position of a rising edge of the electron energy loss spectrum extracted from each of the measured portions matches the result obtained by the photoelectron spectroscopy.

According to the embodiment of the present invention, after the multipole lenses 11, 12 provided in the electron spectroscope are adjusted for the optimal conditions, the spectral image is acquired. However, even when the multipole lenses 11, 12 are not adjusted, the same spectrum correction can be performed.

The present invention made by the present inventors is described above according to the embodiment. However, the present invention is not limited to the embodiment. The present invention may be modified and changed without departing from the spirit and scope of this invention.

While the invention has been described in its preferred embodiments, it is to be understood that the words which have been used are words of description rather than limitation and that changes within the purview of the appended claims may be made without departing from the true scope and spirit of the invention in its broader aspects.

Figure 2A:
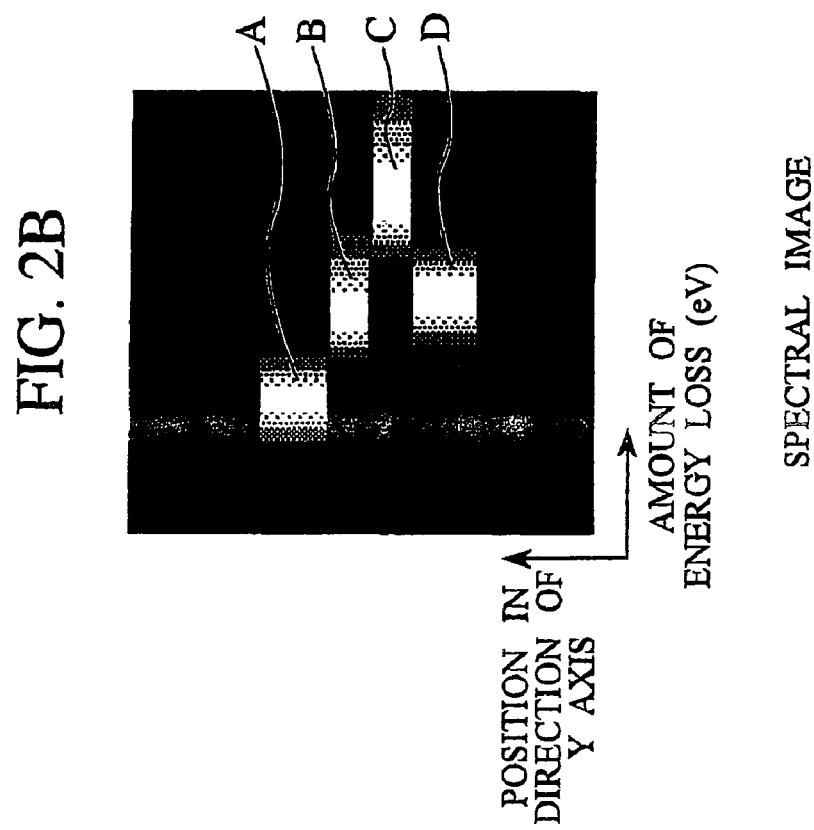
FIGS. 2A and 2B are diagrams showing a transmission electron microscope image and a spectral image, respectively.
Figure 2B:
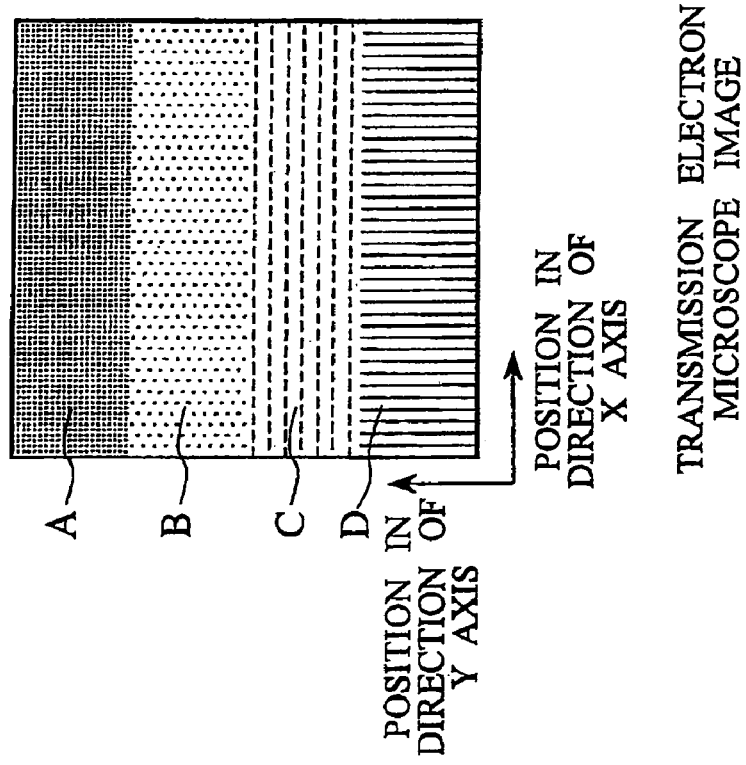

FIG. 1
x axis
y axis
Energy dispersion axis
FIG. 2A
Transmission electron microscope image
Position in direction of y axis
Position in direction of x axis
FIG. 2B
Spectral image
Position in direction of y axis
Amount of energy loss (eV)
FIG. 3
S101 Start
S102 Acquire standard spectral image
S103 Extract spectrum from standard portion S104 Extract spectrum from each measured portion different from standard portion
S105 Compare spectrum extracted from standard portion and spectrum extracted from each measured portion, calculate difference between spectra, and store calculated difference in spectrum correction system
S106 Measure spectral image acquired from sample to be analyzed
S107 Extract spectrum from each measured portion included in spectral image acquired from sample to be analyzed
S108 Correct spectrum extracted from each measured portion included in spectral image acquired from sample to be analyzed based on difference stored in spectrum correction system
S109 Store corrected spectrum in data storage device
FIG. 4
Amount of energy loss
Position in direction of y axis
Amount of energy loss
FIG. 5
41 Oxide silicon layer
41 Nitride silicon layer
41 Oxide silicon layer
42 Silicon substrate

What is claimed is:

1. A method for correcting an electron energy loss spectral image acquired by a transmission electron microscope having an electron spectroscope, the method comprising steps of:
   acquiring a two-dimensional standard spectral image with a first axis representing the amount of an energy loss and a second axis representing positional information;
   comparing a spectrum extracted from the standard spectral image at a standard position with a spectrum extracted from the standard spectral image at each position other than the standard position and calculating correction information at each position based on a difference between the spectrum at the standard position and the spectrum at each position other than the standard position, the difference based on a zero loss spectral image or an electron energy loss spectral image acquired from a sample to be analyzed;
   acquiring an electron energy spectral image from the sample;
   correcting the spectrum of the spectral image from the sample at each position based on the correction information.

2. The method according to claim 1, wherein
   the standard spectral image is at least one of a zero loss spectral image and an electron energy spectral image acquired from a reference sample made of a single type of composition.

3. The method according to claim 1, further comprising the steps of:
   storing the calculated correction information in a storage device; and
   correcting a spectrum for each piece of the positional information included in the electron energy loss spectral image based on the stored correction information.

4. A transmission electron microscope comprising:
   an electron gun for emitting an electron beam;
   a convergent lens group for causing the electron beam emitted by the electron gun to converge;
   an imaging lens group for imaging the electron beam after the electron beam passes through a sample;
   an image detector for detecting an image of the electron beam;
   a view field restriction slit for selecting an area that is to be observed and is included in the sample;
   an electron spectroscope for spectrally decomposing the electron beam based on the amount of energy of the electron beam after the electron beam passes through the sample;
   a spectrum correction system; and
   a data storage device, wherein:
   the electron spectroscope outputs a spectral image acquired by setting a focal point of the electron beam focused in a energy dispersion direction on a plane and by setting another focal point of the electron beam focused in a direction perpendicular to the energy dispersion direction on another plane,
   the spectrum correction system:
      compares a spectrum extracted from a standard spectral image at a standard position with a spectrum extracted from the standard spectral image at each position other than the standard position,
      calculates correction information at each position based on a difference between the spectrum at the standard position and the spectrum at each position other than the standard position, the difference based on a zero loss spectral image or an electron energy loss spectral image acquired from a sample to be analyzed, and
      corrects the spectrum of the spectral image from the sample at each position based on the correction information, and
   the data storage device stores the corrected spectrum therein.

5. The transmission electron microscope according to claim 4, wherein
   the standard spectral image is a zero loss spectral image or an electron energy loss spectral image acquired from a reference sample made by a single type of composition.

6. The transmission electron microscope according to claim 4, further comprising a spectrum difference calculation button to cause the spectrum correction system to start to correct a spectrum included in the spectral image acquired from the sample.

7. The transmission electron microscope according to claim 4, further comprising a spectrum area selection tool capable of arbitrarily setting the standard portion of the standard spectral image.

* * * * *